United States Patent
Isgar

(10) Patent No.: US 11,806,147 B2
(45) Date of Patent: *Nov. 7, 2023

(54) MOOD AGGREGATION SYSTEM

(71) Applicant: Charles Isgar, Scottsdale, AZ (US)

(72) Inventor: Charles Isgar, Scottsdale, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/149,360

(22) Filed: Jan. 3, 2023

(65) Prior Publication Data

US 2023/0148926 A1 May 18, 2023

Related U.S. Application Data

(63) Continuation of application No. 17/169,794, filed on Feb. 8, 2021, now Pat. No. 11,540,758.

(60) Provisional application No. 62/971,121, filed on Feb. 6, 2020.

(51) Int. Cl.
| | |
|---|---|
| *A61B 5/16* | (2006.01) |
| *G16H 10/60* | (2018.01) |
| *G16H 10/20* | (2018.01) |
| *G06V 40/16* | (2022.01) |

(52) U.S. Cl.
CPC ............ *A61B 5/165* (2013.01); *G06V 40/176* (2022.01); *G16H 10/20* (2018.01); *G16H 10/60* (2018.01)

(58) Field of Classification Search
CPC ........ A61B 5/165; G16H 40/67; G16H 50/70; G16H 50/30; G16H 50/20; G16H 15/00; G16H 10/60; G16H 10/20
USPC ........................................................... 705/3
See application file for complete search history.

(56) References Cited

U.S. PATENT DOCUMENTS

2011/0304629 A1* 12/2011 Winchester ............. G06T 13/40
345/473
2015/0370994 A1 12/2015 Madan et al.

FOREIGN PATENT DOCUMENTS

WO 2020115747 6/2020

OTHER PUBLICATIONS

Taggart et al., Determining Emotions via Facial Expression Analysis Software, CSIS, Pace University, May 6, 2016.

* cited by examiner

*Primary Examiner* — Rachelle L Reichert
*Assistant Examiner* — Teresa S Williams
(74) *Attorney, Agent, or Firm* — Schmeiser, Olsen & Watts LLP

(57) ABSTRACT

Described is a mood aggregation system. The system includes a server having a memory storing user information and a user computing device coupled to the server. The server may be programmed to automatically generate a mood request with response capabilities and send the request to the user computing device for display in response to the user computing device accessing the system. The server may also be programmed to receive and store mood data sent from the user computing device, wherein the mood data comprises a mood selection, a time the mood data was sent and a location of the user computing device when sending the mood data. The user may send a request for a report that is received and stored in the server for a user associated with the user computing device and automatically access the stored mood data and generate a report responsive to the report request.

5 Claims, 15 Drawing Sheets

MOOD AGGREGATION SYSTEM

CROSS REFERENCE TO RELATED APPLICATION

This application is a Continuation of U.S. patent application entitled "MOOD AGGREGATION SYSTEM," Ser. No. 17/169,794, filed Feb. 8, 2021, which claims priority to U.S. Provisional patent application entitled "MOOD AGGREGATION SYSTEM," Ser. No. 62/971,121, filed Feb. 6, 2020, the disclosures of which are hereby incorporated entirely herein by reference.

BACKGROUND OF THE INVENTION

Technical Field

This invention generally relates to a system for gathering data regarding moods, and more specifically to a mood aggregation system for receiving and aggregating mood data, including time of day, day of week, location and the like associated with users' moods for analysis and reporting.

State of the Art

Moods throughout a day are often consistently changing. The moods of individuals affect much of what they do, how productive they are, what they eat, and the like. There currently does not exist a system that can gather and track such information. Further, there is not a way to search through such gathered and tracked information in order to draw conclusions from a historical collection of moods throughout the days.

Accordingly, what is needed is a mood aggregation system for receiving and aggregating mood data, including time of day, day of week, location and the like associated with users' moods for analysis, reporting and/or sharing.

SUMMARY OF THE INVENTION

An embodiment includes a mood aggregation system for receiving and aggregating mood data, including time of day, day of week, location and the like associated with users' moods for analysis and reporting.

An embodiment includes a mood aggregation system comprising: a server having a memory storing user information; and a user computing device coupled to the server, wherein the server is programmed to: automatically generate a mood request with response capabilities and send the mood request to the user computing device for display in response to the user computing device accessing the system; receive and store mood data sent from the user computing device, wherein the mood data may comprise a mood selection, a time the mood selection was sent, and a location of the user computing device when sending the mood selection; receive a report request of mood data stored for a user associated with the user computing device; and automatically access the stored mood data and generate a report responsive to the report request. The mood selection may comprise at least two moods. There may be a distinction between the at least two moods. The at least two moods may comprise excited, good, average, bad and terrible. The mood data may be paired with other collected data. The other collected data may be health monitoring data and/or daily event schedule data. The user computing device may be a mobile computing device. The mobile computing device may be wearable. The mobile computing device may comprise a mood app installed on the mobile computing device and operable on the mobile computing device. The mood app operating on the mobile computing device may provide a user interface for the mood selection. The mobile computing device may further comprise a camera and wherein the user interface operates to utilize the camera of the mobile computing device to capture an animation of a user's face, Another embodiment includes a mood aggregation system comprising a server having a memory storing user information; and a plurality of user computing devices, each of the plurality user computing devices coupled to the server, wherein the server is programmed to: automatically generate a mood request with response capabilities and send the mood request to each of the plurality of user computing devices for display, in response to each of the plurality of user computing devices accessing the system; receive and store mood data sent from each of the plurality of user computing devices, wherein the mood data comprises a mood selection, a time the mood data was sent and a location of each of the plurality of user computing devices when sending the mood data; receive a report request of mood data stored for each user associated with each of the plurality of user computing devices; and automatically access the stored mood data and generate a report responsive to the report request. The mood aggregation system may further comprise a reward system to reward each of the users for utilization of the mood aggregation system to collect and share the mood data. The mood selection may comprise at least two moods. There may be a distinction between the at least two moods. The at least two moods may comprise excited, good, average, bad and terrible. The mood data may be paired with other collected data. The other collected data may be health monitoring data and/or daily event schedule data. The user computing device may be a mobile computing device. The mobile computing device may be wearable. The mobile computing device may comprise a mood app installed on the mobile computing device and operable on the mobile computing device. The mood app operating on the mobile computing device may provide a user interface for the mood selection.

The foregoing and other features and advantages of the invention will be apparent to those of ordinary skill in the art from the following more particular description of the invention and the accompanying drawings.

BRIEF DESCRIPTION OF THE DRAWINGS

A more complete understanding of the present invention may be derived by referring to the detailed description and claims when considered in connection with the Figures, wherein like reference numbers refer to similar items throughout the Figures, and:

DETAILED DESCRIPTION OF EMBODIMENTS OF THE INVENTION

Embodiments of the present invention relate to a mood aggregation system for receiving and aggregating mood data, including time of day, day of week, location, and the like, associated with users' moods for analysis and reporting. The system may include the use of a mobile application operating on a user computing device that may be a mobile computing device like a smartphone, a tablet, a wearable, and the like; and/or the system may operate on any type of computing device as a downloadable application or even as a web application.

Figure 1:
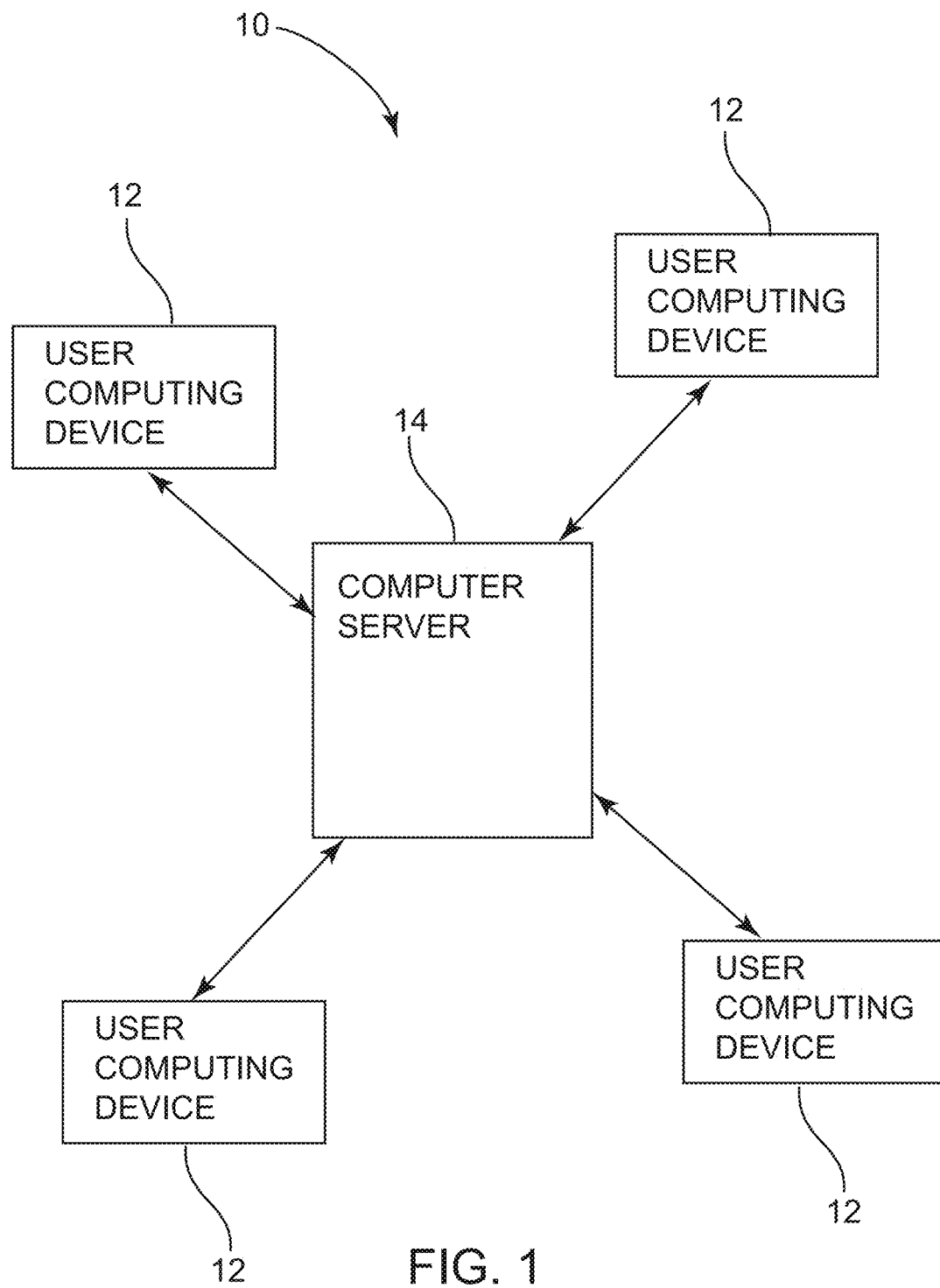
FIG. 1 is a diagrammatic view of a mood aggregation system according to an embodiment.
Figure 2:
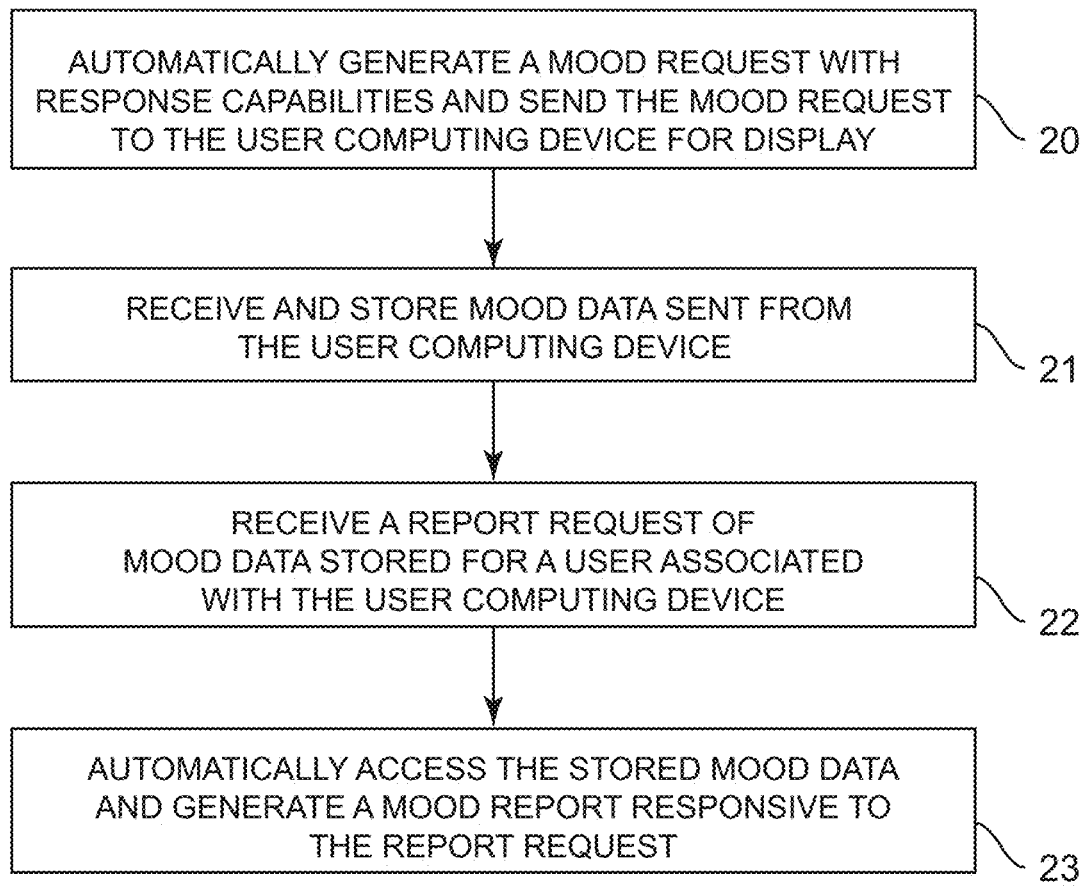
FIG. 2 is a flowchart of programmed instructions executed by a server of a mood aggregation system according to an embodiment.

FIGS. 1-2 show an embodiment of a mood aggregation system 10. FIG. 1 shows a diagram of a mood aggregation system 10. FIG. 2 shows a flow chart of programming of a system 10. In embodiments, a user includes any individual who is seeking to track moods throughout a day, over extended periods of time and/or an ongoing basis.

FIG. 1 depicts an embodiment of a mood aggregation system 10. The system 10 may include user computing device(s) 12 and a server 14, wherein each user computing device 12 is coupled to the computer server 14. This coupling may be a network connection, such as a wireless connection through an Internet connection, a Wi-Fi connection, a Bluetooth connection or the like, wherein the user computing devices 12 may communicate with and receive communication from the server 14. The user computing device 12 may be a desktop computer, a laptop, a tablet, a smartphone, a wearable device, and the like. The server 14, in some embodiments, may be a computer server or a cloud-based infrastructure architecture.

The server 14 may include a memory storing various data. The memory of the server 14 may store user information, such as demographic information, and may further store mood data, given and received, relating to a user from the user computing device 12 and associated with the user information corresponding to the user computing device 12 sending the mood data. The server 14 may operate to aggregate the mood data in a mood database of the memory of the server 14.

The user computing device 12 may be coupled to the server 14, and, referring to FIG. 2, the server 14 may be programmed to automatically generate a mood request with response capabilities and send the mood request to the user computing device for display (Step 20), in response to the user computing device accessing the system; receive and store mood data sent from the user computing device (Step 21), wherein the mood data comprises a mood selection, a time the mood data was sent and a location of the user computing device when sending the mood data; receive a report request of mood data stored for a user associated with the user computing device (Step 22); and automatically access the stored mood data and generate a report responsive to the report request (Step 23). The server 14 may be programmed to perform any of the functions that will be discussed below in greater detail with regard to functionality of the system 10.

Referring to the drawings again, FIGS. 3A-3I depict various interfaces viewable with a user computing device 12 that may be available in an embodiment of the mood aggregation system 10. FIGS. 3A-D depict a user computing device 12 operating an app of the mood aggregation system 10 to enter moods. The interface 30 includes several different elements that may comprise mood selections 32, comment box 34, photo button 36 and a send button 38. In operation, the user may select one of the mood selections 32 such as, but not limited to, excited, good, average, bad and terrible. It will be understood that other descriptors may be used so long as there is a distinction between moods. Further, while 5 moods are shown, it will be understood that any number of moods can be utilized, so long as there are at least two moods. The comment box 34 may be utilized to enter text associated with the mood. Further, the photo button 36 may activate the camera of the device 12 and a photo may be inserted into the comment box 34 to show an individual or an item or a location associated with the mood selected. The comment box 34 may include a time stamp. It will be understood that the mood selection may be sent with or without comments. Further still, it will be understood that the mood is part of the mood data sent from the user computing device 12 to the server 14, wherein the mood data includes the mood selection, a time and a location associated with the selection of and sending of the mood to the server 14.

Figure 3A:
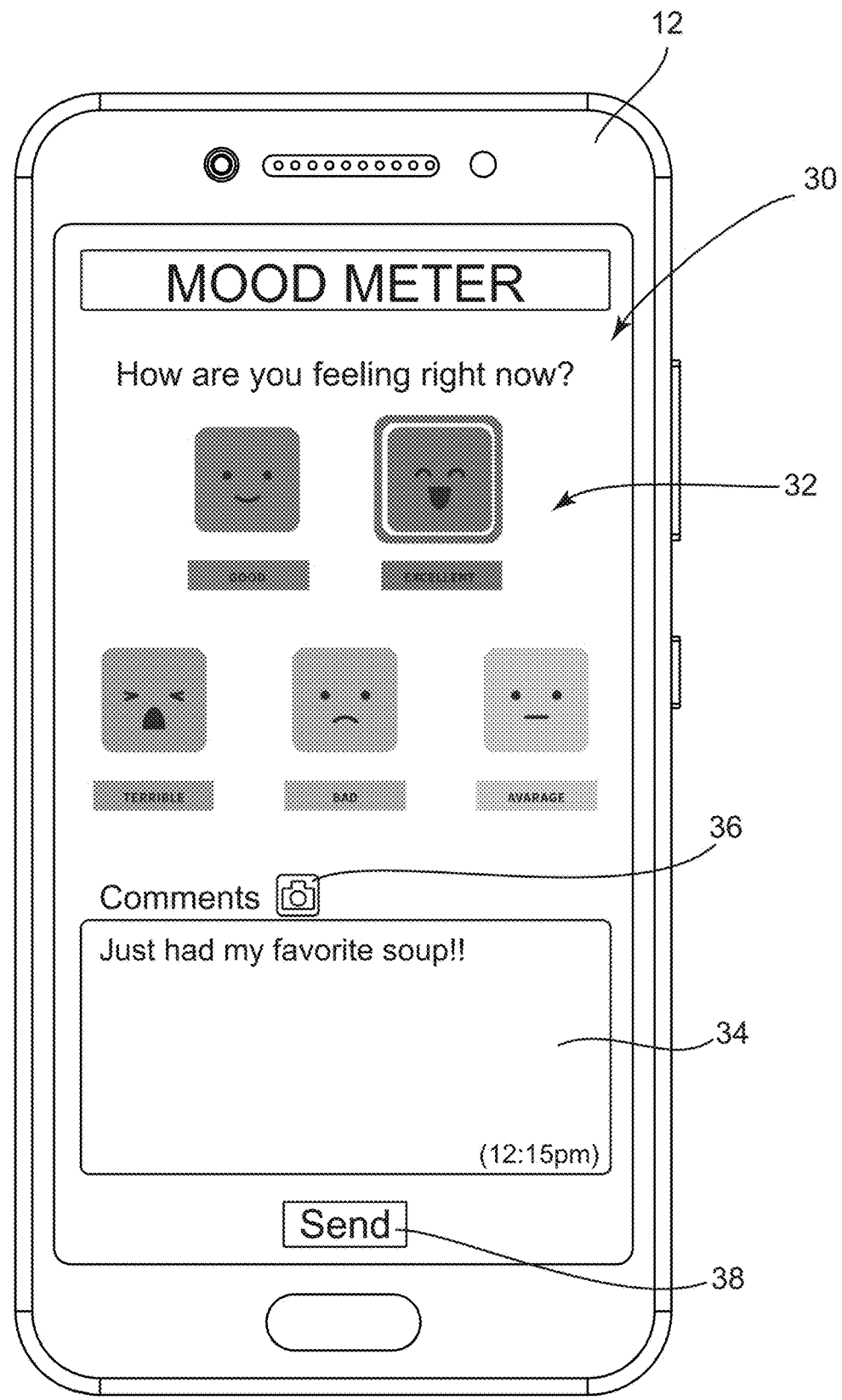
FIG. 3A depicts a user computing device operating a mood aggregation system to enter a user's mood in one time of day according to an embodiment.
Figure 3B:
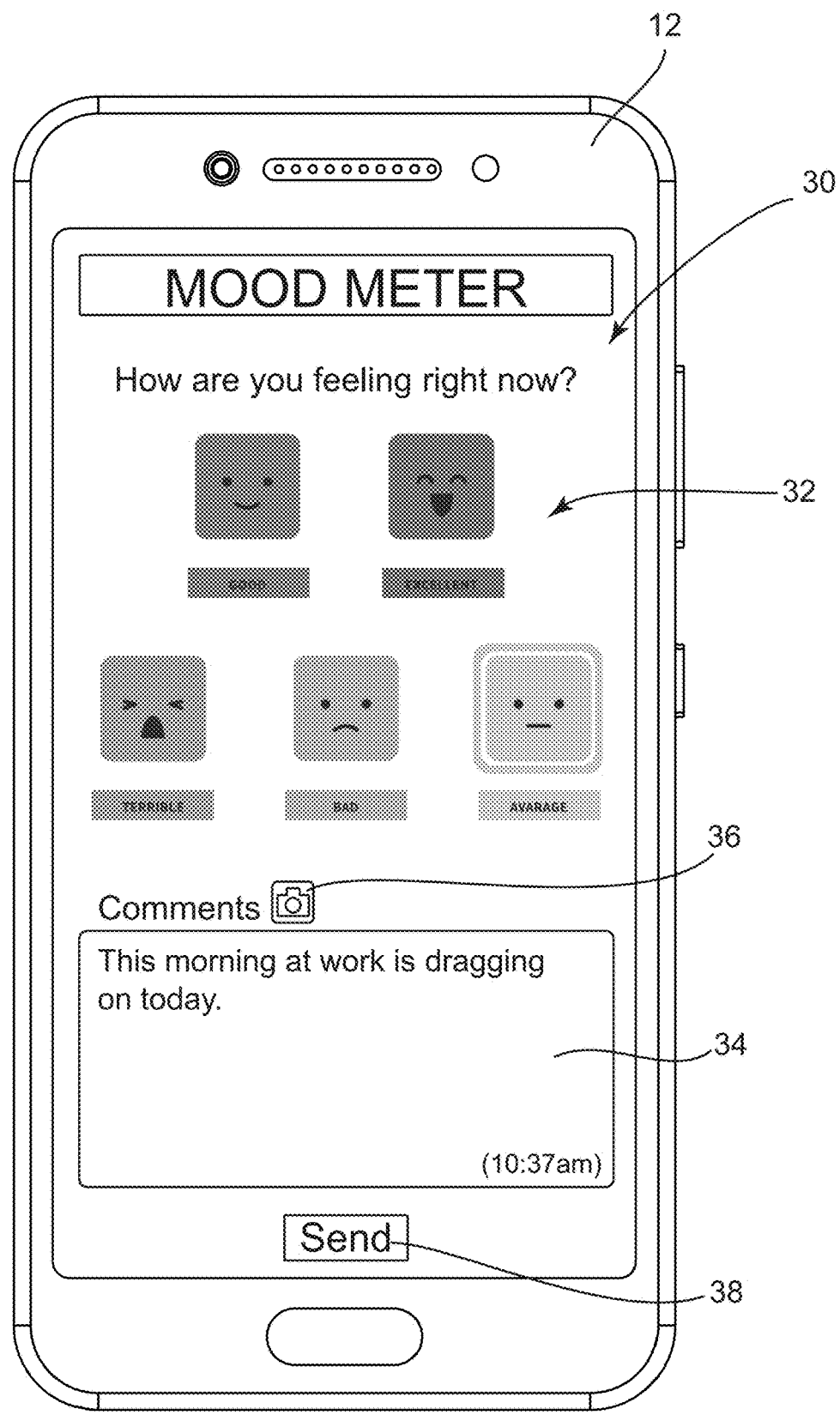
FIG. 3B depicts a user computing device operating a mood aggregation system to enter a user's mood in another time of day according to an embodiment.
Figure 3C:
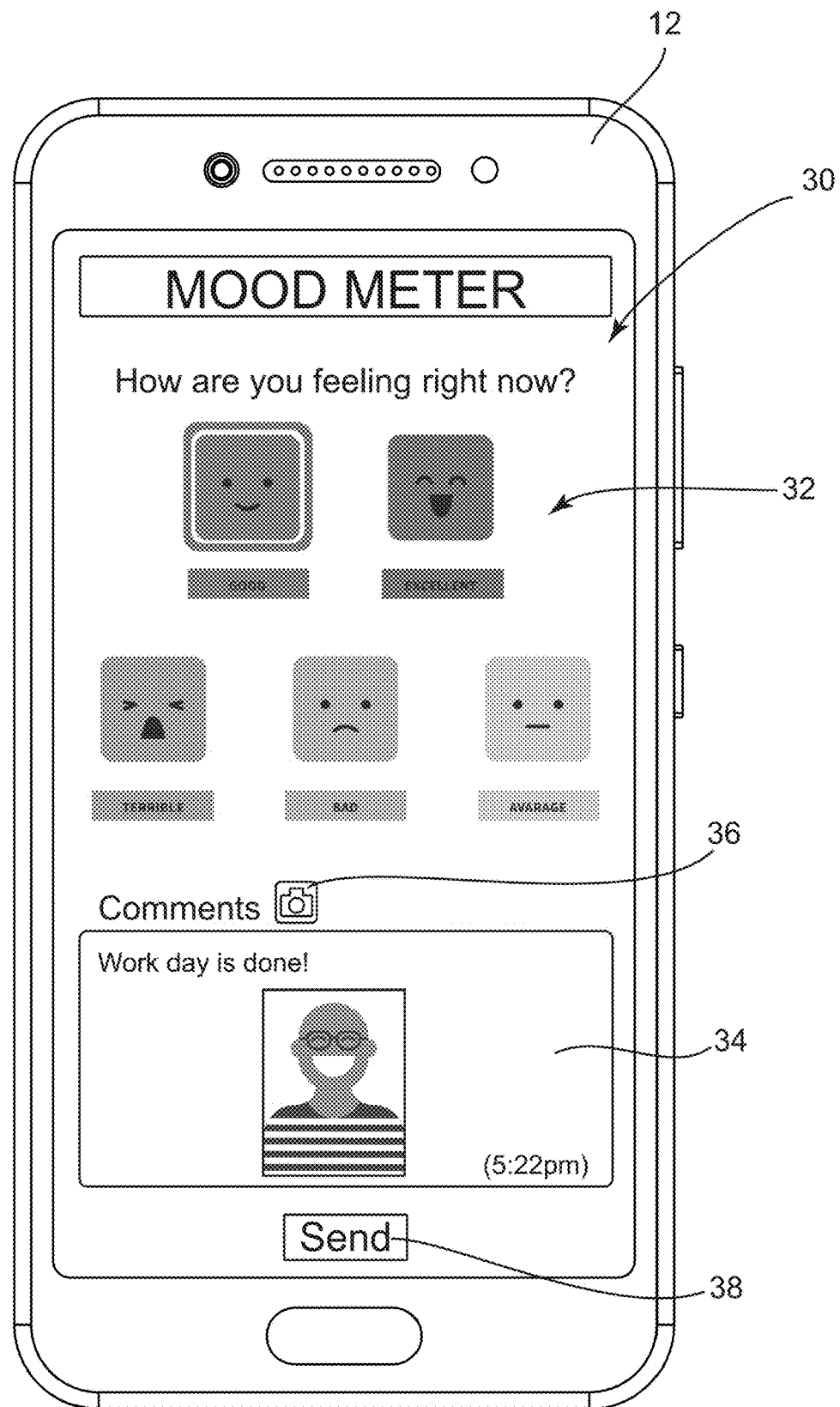
FIG. 3C depicts a user computing device operating a mood aggregation system to enter a user's mood in yet another time of day according to an embodiment.
Figure 3D:
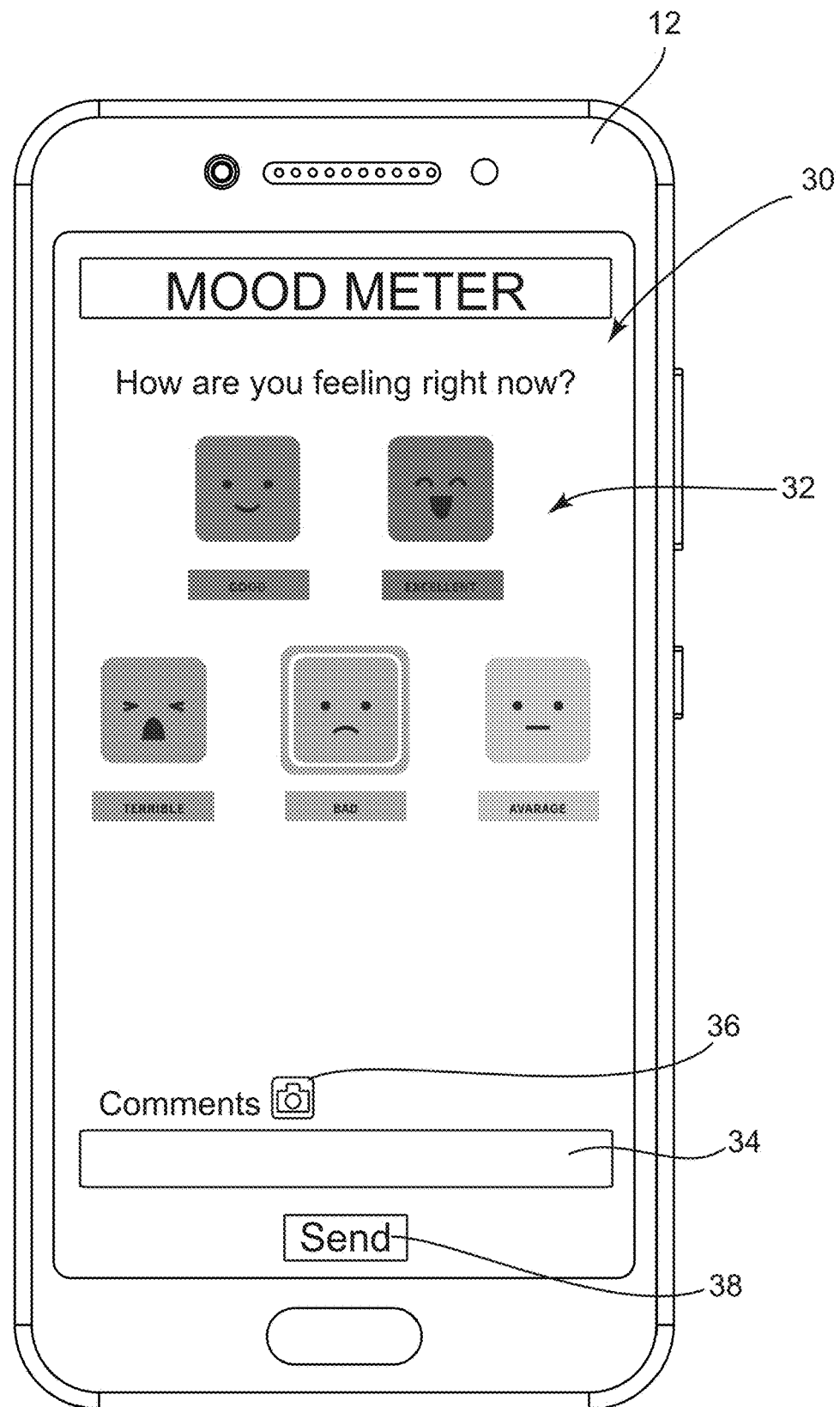
FIG. 3D depicts a user computing device operating a mood aggregation system to enter a user's mood in yet another time of day according to an embodiment.
Figure 3E:
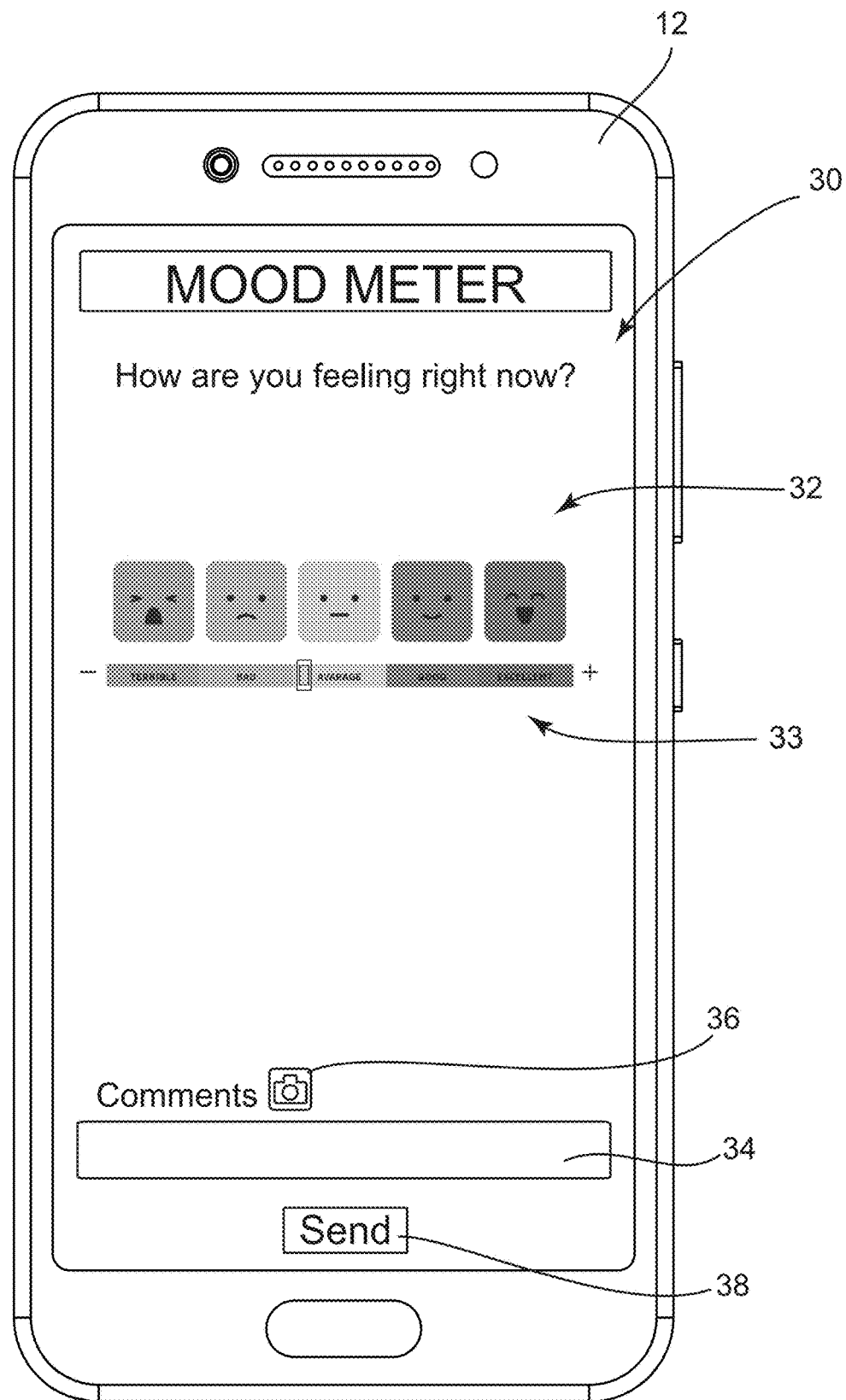
FIG. 3E depicts a user computing device operating a mood aggregation system to enter a user's mood with another type of user interface according to an embodiment.
Figure 3F:
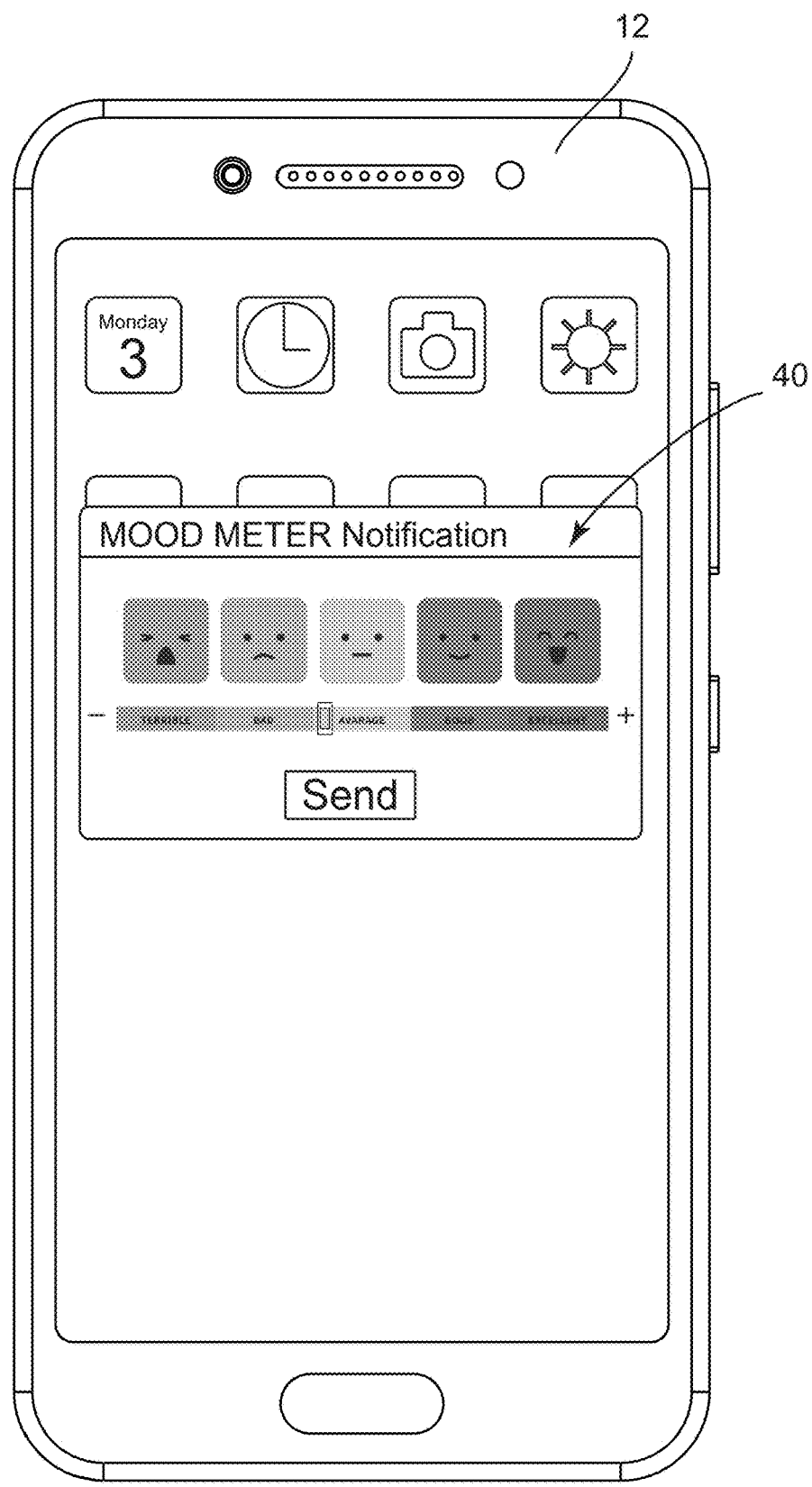
FIG. 3F depicts a user computing device operating a mood aggregation system to enter a user's mood in a notification window according to an embodiment.

In some embodiments, as depicted in FIGS. 3E and 3F, the interface 30 may include mood selections 32 that include a slider bar 33 in order to more specifically select a mood. This allows for more accurate selection of moods by the user. It may be done by the user interface 30 or through a notification window 40 that is operated over other interfaces of the user device 12.

Figure 3G:
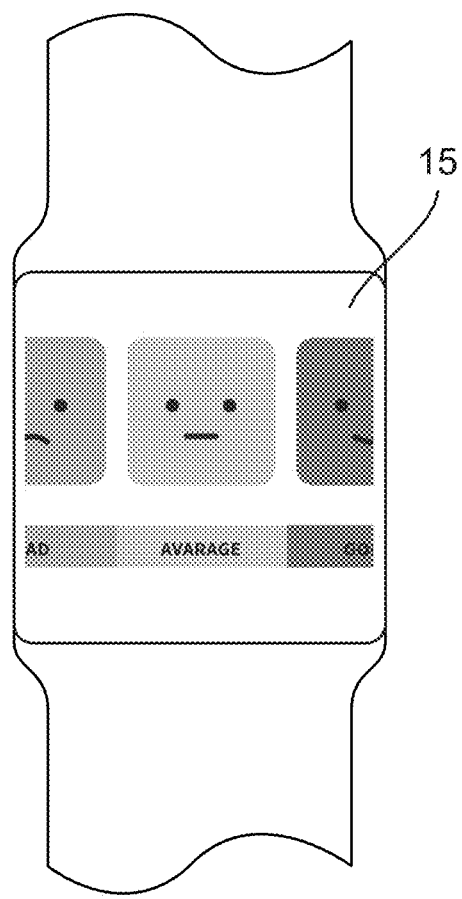
FIG. 3G depicts a smartwatch operating to enter a user's mood as part of a mood aggregation system according to an embodiment.
Figure 3H:
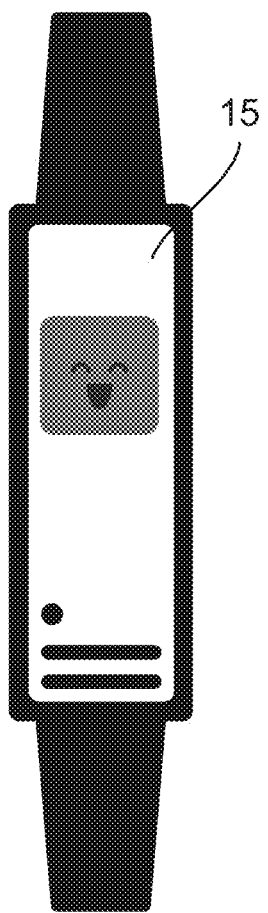
FIG. 3H depicts a fitness tracker type wearable operating to enter a user's mood as part of a mood aggregation system according to an embodiment.
Figure 3I:
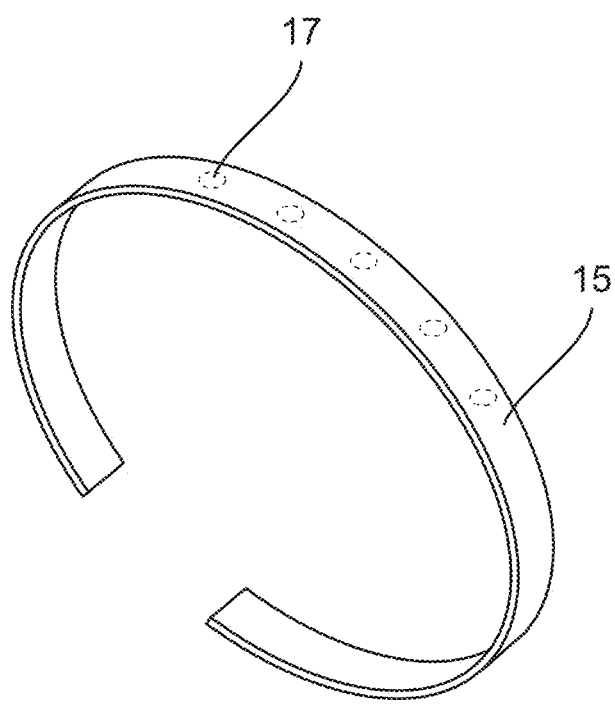
FIG. 3I depicts a dedicated wearable operating to enter a user's mood as part of a mood aggregation system according to an embodiment.

Other user devices 15 are shown in FIGS. 3G-3I. As shown in FIG. 3G, the user device 15 may be connected to the server 14 through an intermediate device, such as user computing device 12. The user device 15 may be a smartwatch as shown in FIG. 3G, wherein the smartwatch may operate an app on the smartwatch that communicates with a corresponding app operating on the user computing device 12. The user device 15 may be a fitness tracker as shown in FIG. 3H, wherein the fitness tracker may operate an app on the fitness tracker that communicates with a corresponding app operating on the user computing device 12. The user device 15 may be a wearable 15 such as a fashion wearable, wherein there are separate inputs 17, each input corresponding to a particular mood, as shown in FIG. 3I, wherein the wearable may operate to communicate with a corresponding app operating on the user computing device 12, wherein depressing or activating an input for a mood results in the app operating on the user computing device 12 to send the mood to the server 14. The wearable in FIG. 3I may be fashionable jewelry or the like that is less obvious as to what the device is used for and can be used when fashion is important to the user. It is also contemplated that all of these devices for input can be utilized at various times by a user to enter his or her mood.

Figure 4A:
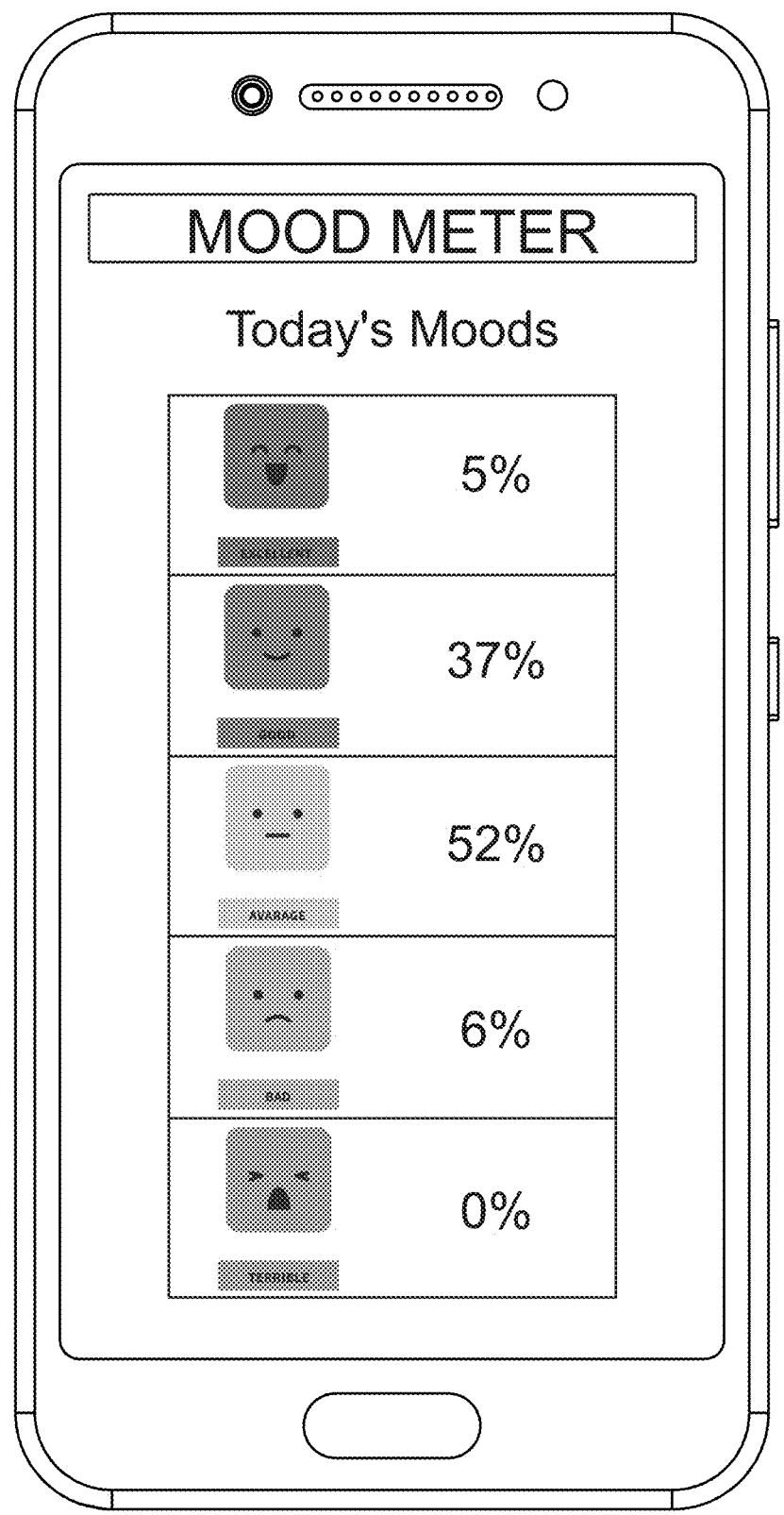
FIG. 4A depicts a user computing device operating a mood aggregation system depicting moods in a particular day according to an embodiment.
Figure 4B:
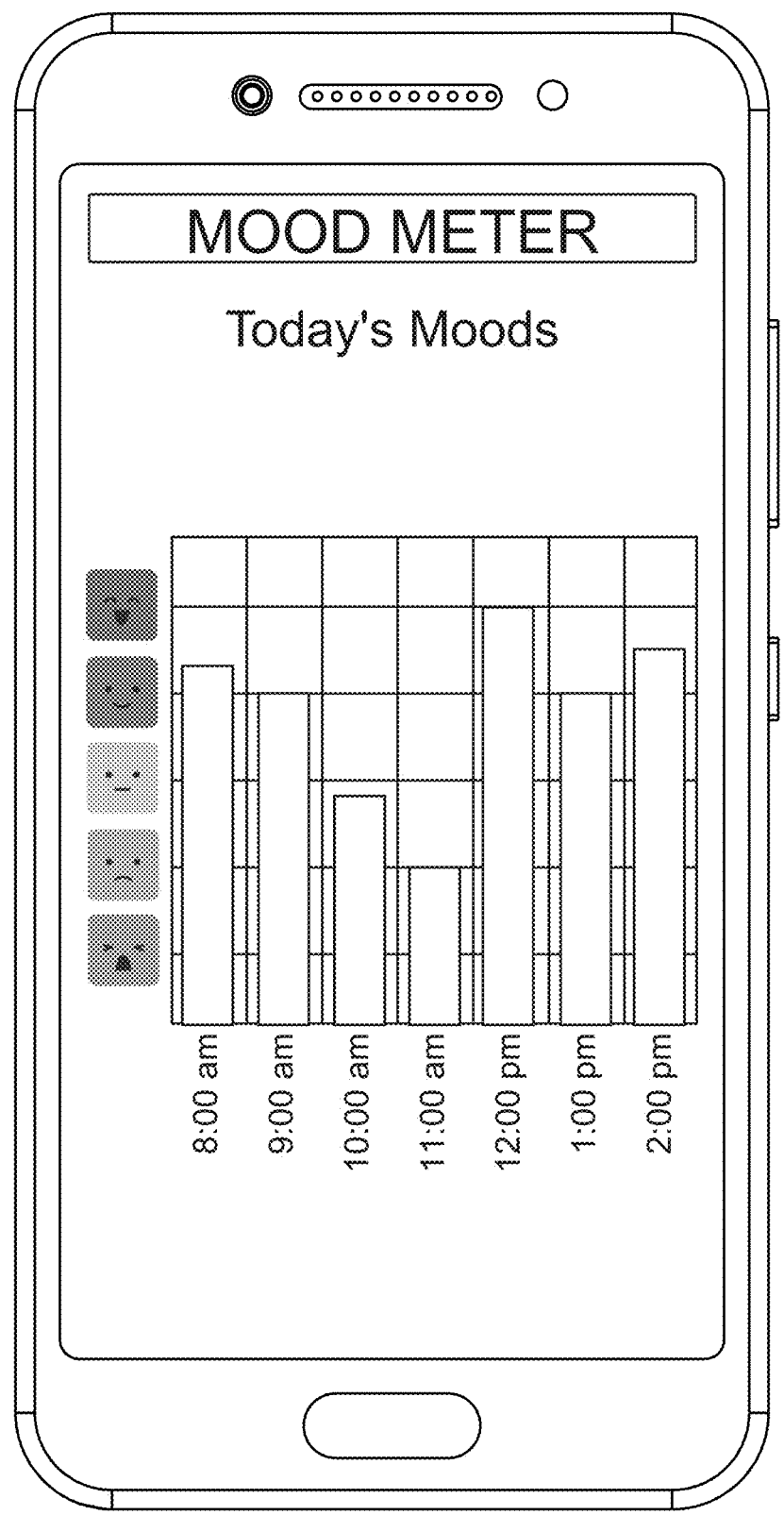
FIG. 4B depicts a user computing device operating a mood aggregation system depicting moods in a particular day according to an embodiment.

The system 10 may allow a user to obtain historical mood data through requesting a report. For example, and without limitation, a user may request a report for his or her own mood on a particular day, as depicted in FIGS. 4A and 4B. The report may include a percentage of time over the day a user had each mood as depicted in FIG. 4A. The report may include the user's moods throughout the day as depicted in FIG. 4B. While not shown, the report may include the number of times a mood selection was entered during each hour of a day, the locations and moods, the comments and moods and any number of reports based on the mood data sent from the user computing device to the server. These reports may be for a day (as shown in the drawings), multiple days, a week, a month, multiple months, a year, the same month over a selected number of years and the like. The reports may also have the ability to include other data collected by the user computing device, such as heart rate, other health data, weather, and the like.

Figure 5:
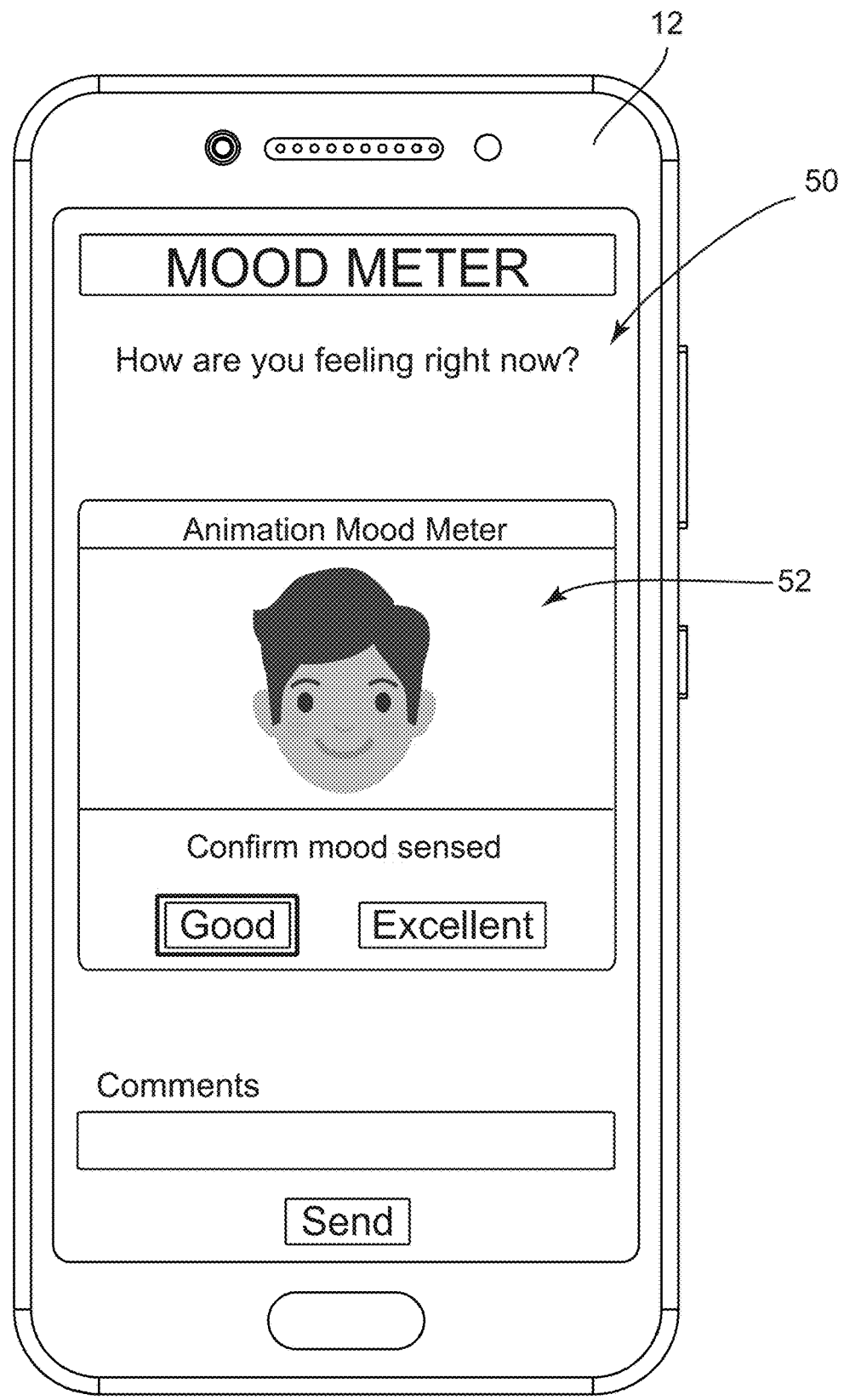
FIG. 5 depicts a user computing device operating a second embodiment of a mood aggregation system to enter a user's mood with an animation user interface according to an embodiment.

A second embodiment of the system 10 may include an app operating on a user computing device 12 having a user interface 50, as shown in FIG. 5. The user interface 50 may operate to utilize a camera of the user computing device 12 to capture an animation of the user's face, wherein the user may make a facial expression consistent with the user's mood as depicted in box 52. The user interface can display the animated facial expression of mood and, utilizing facial recognition software that includes artificial intelligence through self-learning software, determine the mood based on the facial expression presented in the animated capture of the user's face. The user computing device 12 may display, on user interface 50, possible selections based on the interpretation of the facial expression. The user may confirm by selecting the mood corresponding to the facial expression. The user interface may send this data to the server 14 and historical data of animated facial expressions of moods for a user may be stored. The system 10 operates to learn from the historical data to more accurately determine the mood based on the facial expression. The system 10 can fine tune the facial analysis based on the learning of the software so that, in embodiments, the system 10 may not need confirmation of the mood from the user.

Figure 6:
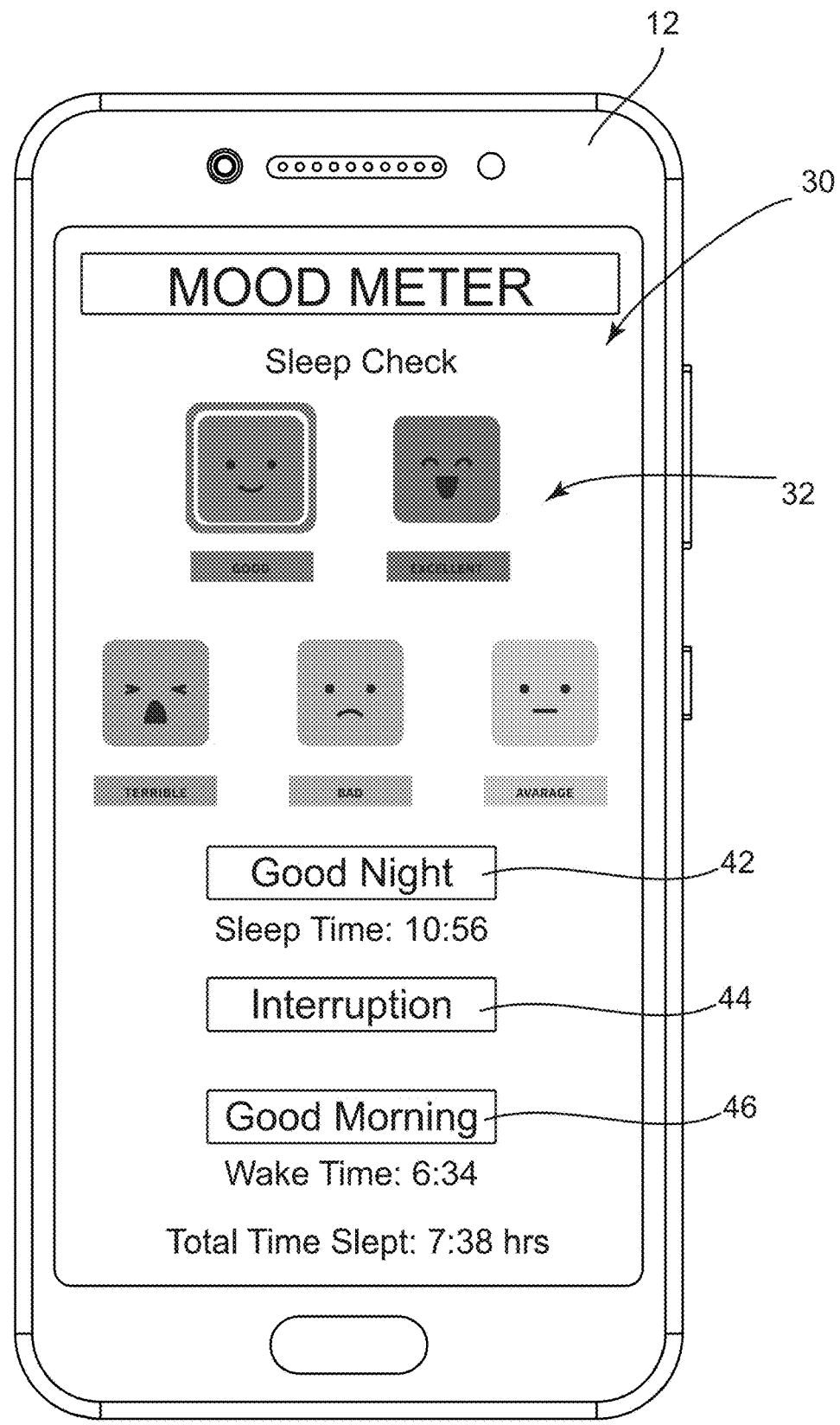
FIG. 6 depicts a user computing device operating a mood aggregation system to enter a user's mood at bed time and waking time according to an embodiment.

Referring further to the drawings, FIG. 6 depicts a user computing device 12 operating an app may display a user interface 30 for signing out at the end of a night and then signing in in the morning. The user interface 30 allows the user to engage a goodnight button 42 to sign out of the system wherein the goodnight button sends mood data to the server 14. The user may then engage the system in the middle of the night or during the user's scheduled sleep time if he or she wakes by selecting a mood and then engaging the interruption button 44. Further, as the user awakes in the morning or end of the scheduled sleep time, the user may sign into the system by selecting a mood and pressing the good morning button 46. This allows the system 10 to track the mood, sleep time, waking time and any sleep interruptions of a user and determine the mood and trends in mood. Further, the interruptions may be tracked, and moods associated with the sleep interruptions in order to compare with waking moods and sleep time moods. This type of mood data may further be used for other instances, such as sleep studies, health purposes and the like.

Embodiments of the mood aggregation system 10 may be utilized for an individual to collet personal data to create charts and the like in reports for the user's own needs or desired uses. Others may utilize the system and share the data and/or reports with friends through social media posts and the like. In other embodiments, the system may be accessed by third party entities, wherein the aggregated mood data is anonymously provided to a third party entity for study or the like comparing groups of individuals to determine factors that may affect the mood of larger groups of people in certain areas. In some embodiments, data may be collected for groups of people, such as students in a same college class.

In some embodiments, the system may include a reward system to reward users for utilization of the system to collect and share mood data, such as through advertisements for business to see how the mood in certain businesses is affected and to determine how adjustments to the business environment affects mood. The rewards may be coupons, discounts, or the like.

It is anticipated that the interaction with the system 10 may be fun for users and the activity and entry of moods may be extremely high for some individuals throughout a day, ranging from 3-5 up to possibly 1,000 in a day. The system 10 is equipped to handle as many or as little mood data inputs as a user enters throughout a day.

The data may be used to analyze trends in a user's day, trends in a group of people's days, or any other uses for such aggregation of mood data. The user may utilize the mood aggregation data to correspond to other health metrics tracked and logged to better determine overall health of the user or a group of users. Health metrics may include heart rate, blood oxygen level, temperature, electrocardiogram, sleep/wakefulness, calories burned, fitness tracking, steps walked, distance traveled, and so forth. Medical studies may utilize the system as part of their studies and trials. Further, such a system may be incorporated into opinion input, such as real-time reactions for events like awards shows, political debates, and other real-time or near instant feedback scenarios and/or events.

There are many uses of embodiments of the mood aggregation system 10. Such uses may be personal, for sharing in a social manner, for groups of people like students, employees or the like, for self-satisfaction, for health organizations or personal health. The system allows for pairing of mood data with other collected data, such as health monitoring, daily events, and the like. The system can be adapted for specific use at an event or with an audience utilizing the already-built ecosystem of the mood aggregation system 10 to apply to the event or audience.

Embodiments may be available on or through the internet, such as through domain names reserved and owned by Applicant that include mood-meter.com, checkmood.com, moodtick.com and the like.

As will be appreciated by one skilled in the art, aspects of the present invention may be embodied as a system, method, or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wire-line, optical fiber cable, RF, etc., or any suitable combination of the foregoing.

Computer program code for carrying out operations for aspects of the present invention may be written in any combination of one or more programming languages, including an object-oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, cloud-based infrastructure architecture, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The embodiments and examples set forth herein were presented in order to best explain the present invention and its practical application and to thereby enable those of ordinary skill in the art to make and use the invention. However, those of ordinary skill in the art will recognize that the foregoing description and examples have been presented for the purposes of illustration and example only. The description as set forth is not intended to be exhaustive or to limit the invention to the precise form disclosed. Many modifications and variations are possible in light of the teachings above without departing from the spirit and scope of the forthcoming claims.

The invention claimed is:

1. A mood aggregation system comprising:
  a server having a memory storing user information and historical data of animated facial expressions of moods for a user; and
  a user computing device coupled to the server, wherein the server is programmed to:

in response to the user computing device displaying a user interface comprising a mood selection of at least two moods, an animation box, wherein the user computing device further comprises a camera, wherein the user interface operates to utilize the camera of the user computing device to capture an animation of the user's facial expression and display the animation in the animation box, send to the server a capture of the user's facial expression and a selected mood from the at least two moods, store the animated facial expression and selected mood in the memory to create historical data of animated facial expressions for the user, wherein this process is repeated over time to create a larger historical data of animated facial expressions;

automatically generate a mood request with response capabilities and send the mood request to the user computing device for display, in response to the user computing device accessing the system;

send for display on the user computing device an interface for and instruction to utilize the camera of the user computing device to capture an animation of the user's face making a facial expression consistent with the user's mood; and receive and store mood data sent from the user computing device, wherein the mood data comprises the captured animated facial expression, a time the mood data was sent and a location of the user computing device when sending the mood data, wherein utilizing facial recognition software that includes artificial intelligence through self-learning software, determines the mood based on the captured facial expression in comparison with the historical data of animated facial expressions.

2. The mood aggregation system of claim 1, wherein there is a distinction between the at least two moods.

3. The mood aggregation system of claim 2, wherein the at least two moods comprise excited, good, average, bad and terrible.

4. The mood aggregation system of claim 1, wherein the mood data is paired with other collected data.

5. The mood aggregation system of claim 4, wherein the other collected data is health monitoring data and/or daily event schedule data.

* * * * *